US010559077B2

(12) United States Patent
Onimura et al.

(10) Patent No.: US 10,559,077 B2
(45) Date of Patent: Feb. 11, 2020

(54) IMAGE PROCESSING APPARATUS, IMAGE PROCESSING METHOD, AND PROGRAM

(71) Applicant: TERUMO KABUSHIKI KAISHA, Shibuya-ku, Tokyo (JP)

(72) Inventors: Yuuji Onimura, Fujinomiya (JP); Akiyuki Takami, Fukui (JP); Atsushi Sakaoka, Hadano (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 207 days.

(21) Appl. No.: 15/719,837

(22) Filed: Sep. 29, 2017

(65) Prior Publication Data
US 2018/0025481 A1    Jan. 25, 2018

Related U.S. Application Data

(63) Continuation of application No. PCT/JP2016/059088, filed on Mar. 23, 2016.

(30) Foreign Application Priority Data

Mar. 30, 2015  (JP) .................................. 2015-068626

(51) Int. Cl.
*G06K 9/00*     (2006.01)
*G06T 7/00*     (2017.01)
(Continued)

(52) U.S. Cl.
CPC ............ *G06T 7/001* (2013.01); *A61B 5/0066* (2013.01); *A61B 5/0084* (2013.01);
(Continued)

(58) Field of Classification Search
CPC ............ A61B 1/00; A61B 2018/00404; A61B 2018/00577; A61B 5/0084; A61B 5/02007; G06T 2207/30101; G06T 2207/30021
See application file for complete search history.

(56) References Cited

U.S. PATENT DOCUMENTS

| 9,089,331 B2 * | 7/2015 | Rollins ................ A61B 5/0066 |
| 2010/0042084 A1 * | 2/2010 | Nariyuki ............... A61B 5/0066 606/15 |

(Continued)

FOREIGN PATENT DOCUMENTS

| JP | 2008-543511 A | 12/2008 |
| JP | 2010-042182 A | 2/2010 |

(Continued)

OTHER PUBLICATIONS

International Search Report (PCT/ISA/210) dated Jun. 21, 2016, by the Japanese Patent Office as the International Searching Authority for International Application No. PCT/JP2016/059088.

(Continued)

*Primary Examiner* — Avinash Yentrapati
(74) *Attorney, Agent, or Firm* — Buchanan Ingersoll & Rooney PC

(57) ABSTRACT

An image processing apparatus is disclosed, which uses OCT to process a plurality of cross-sectional images obtained by moving an imaging core inside a catheter in an axial direction while rotating the imaging core. Cross-sectional image data is acquired in association with position information in the axial direction when each of the cross-sectional images. A first cross-sectional image in which a disappearance section enabling determination having a disappeared portion of an external elastic membrane included in a vascular tomographic image starts, and a second cross-sectional image in which the disappearance section ends are (Continued)

extracted from the plurality of cross-sectional images. The position information in the axial direction is acquired for the first cross-sectional image and the second cross-sectional image, and an ablation range influenced by ablation at a position associated with the disappearance section is calculated based on a difference in the acquired position information in the axial direction.

20 Claims, 8 Drawing Sheets

(51) Int. Cl.
    *G06T 7/73*     (2017.01)
    *A61B 5/00*     (2006.01)
    *A61B 18/14*     (2006.01)
    *A61B 18/00*     (2006.01)

(52) U.S. Cl.
    CPC ............ *A61B 5/4848* (2013.01); *A61B 5/742* (2013.01); *G06T 7/74* (2017.01); *A61B 18/1492* (2013.01); *A61B 2018/00982* (2013.01); *G06T 2200/24* (2013.01); *G06T 2207/10101* (2013.01); *G06T 2207/30101* (2013.01)

(56) References Cited

U.S. PATENT DOCUMENTS

| | | | | |
|---|---|---|---|---|
| 2011/0245684 A1* | 10/2011 | Onimura | ............. | A61B 5/0066 600/476 |
| 2012/0101372 A1* | 4/2012 | Teramura | ............. | A61B 5/0066 600/425 |
| 2012/0191079 A1* | 7/2012 | Moll | .................... | A61B 5/0084 606/14 |
| 2012/0253184 A1* | 10/2012 | Furuichi | ............. | A61B 5/0066 600/425 |
| 2013/0030295 A1* | 1/2013 | Huennekens | .......... | A61B 6/504 600/440 |
| 2015/0190054 A1* | 7/2015 | Kaneko | .................... | A61B 8/12 600/424 |

FOREIGN PATENT DOCUMENTS

| | | |
|---|---|---|
| JP | 2012-513873 A | 6/2012 |
| JP | 2012-157384 A | 8/2012 |
| JP | 2012-200532 A | 10/2012 |
| WO | WO 2013/099797 A1 | 7/2013 |
| WO | WO 2014/068606 A1 | 5/2014 |

OTHER PUBLICATIONS

Written Opinion (PCT/ISA/237) dated Jun. 21, 2016, by the Japanese Patent Office as the International Searching Authority for International Application No. PCT/JP2016/059088.

* cited by examiner

FIG. 8

| | CROSS-SECTIONAL IMAGE DATA 802 | PULL-BACK POSITION 803 | DISAPPEARANCE GENERATION 804 | ABLATION DEPTH 805 |
|---|---|---|---|---|
| #001 | | | | | 
| #002 | | | | |
| #003 | | | | |
| #004 | | | | |
| #005 | | | | |

801

IMAGE PROCESSING APPARATUS, IMAGE PROCESSING METHOD, AND PROGRAM

CROSS-REFERENCES TO RELATED APPLICATIONS

This application is a continuation of International Application No. PCT/JP2016/059088 filed on Mar. 23, 2016, which claims priority to Japanese Application No. 2015-068626 filed on Mar. 30, 2015, the entire contents of which are incorporated herein by reference.

TECHNICAL FIELD

The present disclosure relates to an image processing apparatus, an image processing method, and a program for processing an optical coherence tomographic image.

BACKGROUND ART

In a case of a patient suffering from intractable hypertension, whose hypertension status is less likely to be improved even after the patient takes an antihypertensive drug, it is understood that the patient can expect blood pressure to be lowered by cutting or damaging a sympathetic nerve present around a renal artery and blocking neurotransmissions.

As a procedure of percutaneously cutting the sympathetic nerve of the renal artery, a technique is known in which a distal portion of a catheter (ablation device) for ablation is inserted into the renal artery so as to ablate the sympathetic nerve from the inside of the renal artery. This type of ablation device has an electrode unit in a distal end of an elongated shaft, and brings the electrode unit into contact with an inner wall of the renal artery. Thermal energy is applied to the sympathetic nerve present around the renal artery, thereby ablating the sympathetic nerve (See JP-T-2012-513873).

It is known that the sympathetic nerve is present around the renal artery. However, the sympathetic nerve irregularly runs through surrounding tissues of the renal artery. Consequently, it can be difficult to recognize which portion of the renal artery is in proximity to the sympathetic nerve. Therefore, in the procedure of cutting the sympathetic nerve, ablation is performed over the entire periphery along the inner wall of the renal artery, thereby more reliably cutting the sympathetic nerve. However, in some cases, an ablation site may undergo tissue degeneration and necrosis or swelling of a vascular wall. Accordingly, the ablation is not performed over the entire periphery of the inner wall at the same position. The thermal energy is applied while the position is moved in an axial direction of the blood vessel, that is, in a spiral shape at a predetermined interval.

In recent years, it has been suggested to use an optical coherence tomography technique in order to accurately recognize a position of the sympathetic nerve of the renal artery when the procedure of cutting the sympathetic nerve of the renal artery is performed. Specifically, for example, a method has been proposed in which a birefringence boundary between the nerve and a muscle or a nerve tissue and a connective tissue is detected using the optical coherence tomography technique so as to determine the position of the nerve of the renal artery. (See International Publication No. WO2013/0099797).

In the procedure of ablating the sympathetic nerve via a lumen wall of the renal artery as described above, the thermal energy is applied to each ablation site for a predetermined time, for example, of approximately 30 seconds to 2 minutes. An operator reads the temperature of the lumen wall of the renal artery and impedance variations between an electrode and a return electrode plate, or between the electrodes, and empirically determines whether the ablation is successful. That is, there has been no way to directly determine an ablation state of the sympathetic nerve. For example, in International Publication No. WO2013/0099797, when the procedure of cutting the sympathetic nerve of the renal artery is performed, the position of the sympathetic nerve of the renal artery can be accurately recognized. However, it is difficult to determine the ablation state of the ablation site after the inner wall of the renal artery is ablated using the thermal energy.

However, in the procedure of cutting the sympathetic nerve of the renal artery, in a case where the sympathetic nerve is insufficiently ablated, a sufficient therapeutic effect cannot be obtained. In a case where the lumen wall of the renal artery is excessively ablated, there is a possibility that complications may be developed with the increased risk. That is, whether or not the sympathetic nerve present around the renal artery is successfully ablated directly leads to the therapeutic effect. Therefore, in order to perform the procedure of cutting the sympathetic nerve present around the renal artery, it is necessary to determine the ablation state of the ablation site of the sympathetic nerve present around the renal artery.

SUMMARY OF THE DISCLOSURE

The present disclosure is made in view of the above-described problems, and enables a user to more accurately recognize an ablation state by using a tomographic image obtained using optical coherence tomography.

In accordance with an exemplary embodiment, an image processing apparatus according to a position embodiment of the present disclosure includes the following configurations. That is, an image processing apparatus is disclosed for using OCT to process a plurality of cross-sectional images obtained by moving an imaging core inside a catheter in an axial direction while rotating the imaging core. The image processing apparatus includes storage means for storing data relating to the cross-sectional images in association with position information in the axial direction when each of the cross-sectional images is acquired, extraction means for extracting a first cross-sectional image in which a disappearance section enabling determination that there is a disappeared portion of an external elastic membrane included in a vascular tomographic image starts, and a second cross-sectional image in which the disappearance section ends, in the plurality of cross-sectional images, and calculation means for acquiring the position information in the axial direction of the first cross-sectional image and the second cross-sectional image from the storage means, and for calculating an ablation range influenced by ablation at a position associated with the disappearance section, based on a difference in the acquired position information in the axial direction.

According to the present disclosure, a tomographic image obtained by means of optical coherence tomography is used, thereby enabling a user to more accurately recognize an ablation state.

An image processing method is disclosed for using OCT to process a plurality of cross-sectional images obtained by moving an imaging core inside a catheter in an axial direction while rotating the imaging core, the method comprising: causing a memory to store data relating to the cross-sectional images in association with position information in the axial direction when each of the cross-sectional images is acquired; extracting a first cross-sectional image in which a disappearance section enabling determination that there is a disappeared portion of an external elastic membrane included in a vascular tomographic image starts, and a second cross-sectional image in which the disappearance section ends, in the plurality of cross-sectional images; and acquiring the position information in the axial direction of the first cross-sectional image and the second cross-sectional image from the memory, and of calculating an ablation range influenced by ablation at a position associated with the disappearance section, based on a difference in the acquired position information in the axial direction.

An image processing method is disclosed for using OCT to process a plurality of cross-sectional images obtained by moving an imaging core inside a catheter in an axial direction while rotating the imaging core, the method comprising: storing data relating to the cross-sectional images in association with position information in the axial direction when each of the cross-sectional images is acquired; extracting a first cross-sectional image in which a disappearance section enabling determination that there is a disappeared portion of an external elastic membrane included in a vascular tomographic image starts, and a second cross-sectional image in which the disappearance section ends, in the plurality of cross-sectional images; and acquiring the position information in the axial direction of the first cross-sectional image and the second cross-sectional image, and for calculating an ablation range influenced by ablation at a position associated with the disappearance section, based on a difference in the acquired position information in the axial direction.

Other features and advantageous effects of the present disclosure will become apparent from the following description with reference to the accompanying drawings. In the accompanying drawings, the same reference numerals will be given to the same or similar configurations.

BRIEF DESCRIPTION OF THE DRAWINGS

The accompanying drawings are incorporated in, configure a part of this specification, and illustrate embodiments according to the present disclosure. Together with the description, the accompanying drawings are used in order to describe principles of the present disclosure.

FIG. 8 is a view illustrating a configuration example of frame data.

DETAILED DESCRIPTION

Hereinafter, each embodiment according to the present disclosure will be described in detail with reference to the accompanying drawings. The embodiments described below are merely preferred specific examples of the present disclosure. Accordingly, technically preferable limitations are imposed in various ways. However, the scope of the present disclosure is not limited to the embodiments unless otherwise the present disclosure is particularly limited in the following description.

Figure 1:
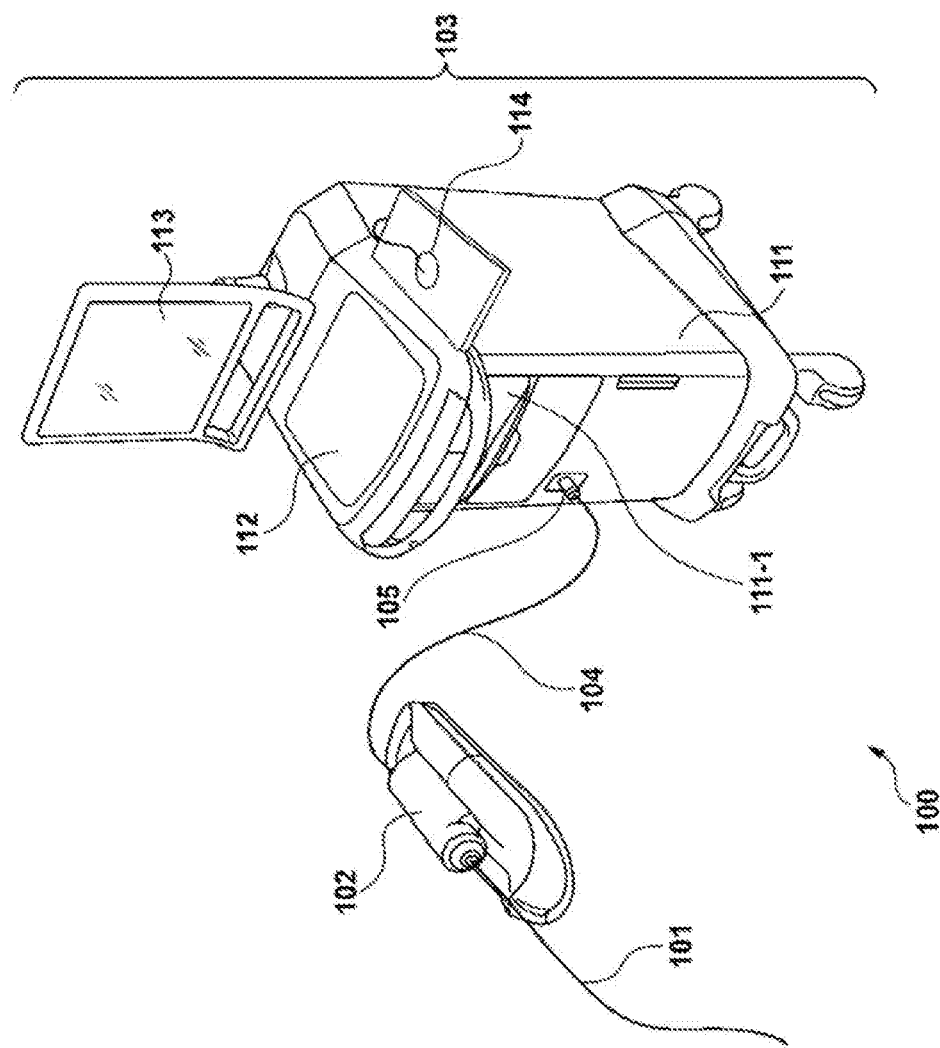
FIG. 1 is a view illustrating an external configuration of an imaging apparatus for diagnosis according to an embodiment.

FIG. 1 illustrates an external configuration of an imaging apparatus for diagnosis 100 using optical interference in the embodiment.

As illustrated in FIG. 1, the imaging apparatus for diagnosis 100 can include a probe 101, a motor drive unit 102, and an operation control apparatus 103. The motor drive unit 102 and the operation control apparatus 103 are connected to each other via a connector 105 by a cable 104 accommodating a signal line and an optical fiber.

In accordance with an exemplary embodiment, the probe 101 is directly inserted into a blood vessel, is movable in a longitudinal direction thereof, and accommodates a rotatable imaging core. A distal end of the rotatable imaging core has a housing for accommodating an optical transceiver which continuously transmits light (measurement light) transmitted from the imaging apparatus for diagnosis 100 into the blood vessel and continuously receives reflected light from the inside of the blood vessel. In the imaging apparatus for diagnosis 100, a state inside the blood vessel is measured using the imaging core.

The probe 101 is detachably attached to the motor drive unit 102, and a built-in motor is driven, thereby regulating the movement in the axial direction inside the blood vessel of the imaging core interpolated into the probe 101 and a rotary operation around the axis. In accordance with an exemplary embodiment, the motor drive unit 102 has a function to move the imaging core in the axial direction inside the catheter to while rotating the imaging core. In addition, the motor drive unit 102 functions as a relay device for a signal exchanged between the optical transceiver in the imaging core and the operation control apparatus 103. In accordance with an exemplary embodiment, the motor drive unit 102 has a function to transmit the measurement light output from the operation control apparatus 103 to the optical transceiver, and to transmit the reflected light from a biological tissue, which is detected by the optical transceiver to the operation control apparatus 103.

When measurement is performed, the operation control apparatus 103 has a function to input various setting values, and a function to process optical interference data obtained by the measurement and to display various blood vessel images.

In the operation control apparatus 103, the reference numeral 111 represents a main body control unit. In accordance with an exemplary embodiment, the main body control unit 111 generates interference light data by causing the reflected light from the imaging core to interfere with reference light obtained by separating the light emitted from a light source, and performs FFT on the interference light data, thereby generating line data facing in a radial direction from a rotation center position. Then, through interpolation processing, a vascular cross-sectional image based on optical interference is generated from the line data.

The reference numeral 111-1 represents a printer and a DVD recorder, which print processing results in the main body control unit 111 and store the processing results as data. The reference numeral 112 represents an operation panel, and a user inputs various setting values and instructions via the operation panel 112. The reference numeral 113 represents a monitor (for example, a liquid-crystal display (LCD)) serving as a display device, which displays various cross-sectional images generated in the main body control unit 111. The reference numeral 114 represents a mouse serving as a pointing device (coordinate input device).

Figure 2:
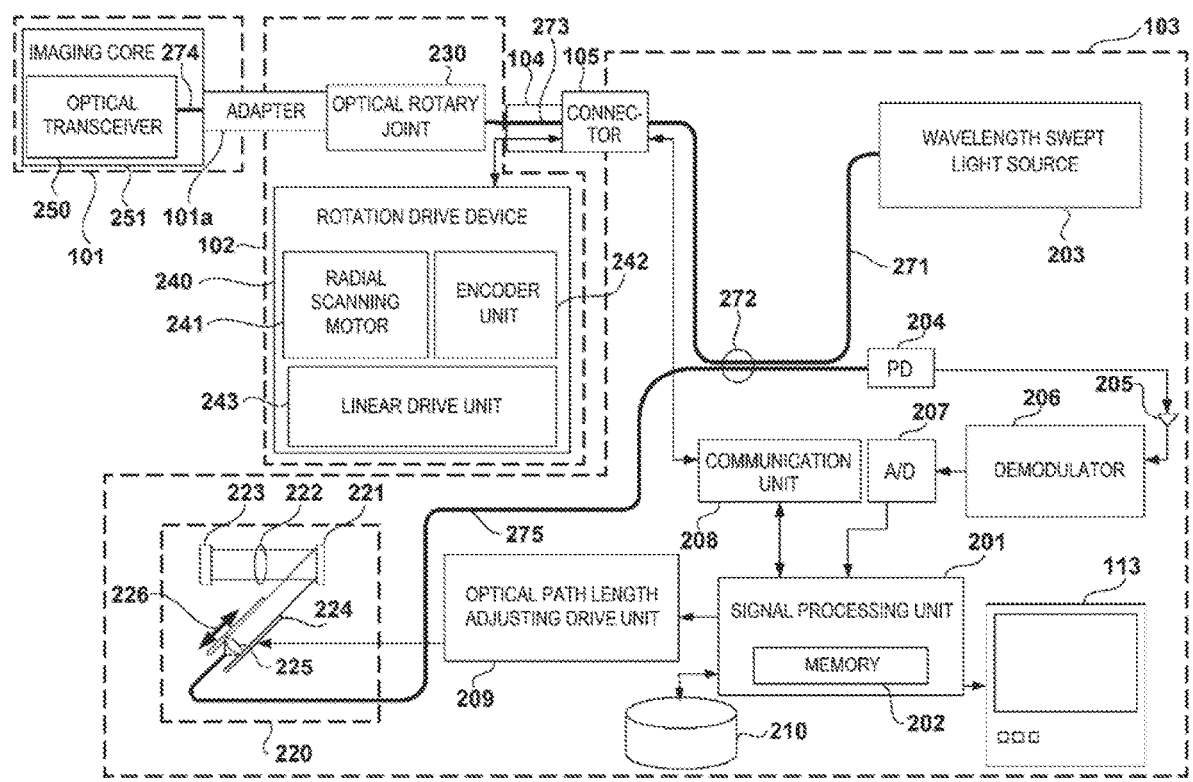
FIG. 2 is a block configuration diagram of the imaging apparatus for diagnosis according to the embodiment.

Next, a functional configuration of the imaging apparatus for diagnosis 100 will be described. FIG. 2 is a block configuration diagram of the imaging apparatus for diagnosis 100. Hereinafter, the functional configuration of wavelength swept source OCT will be described with reference to the drawing.

In the drawing, the reference numeral 201 represents a signal processing unit which controls an entire operation of the imaging apparatus for diagnosis, and is configured to have several circuits including a microprocessor. The reference numeral 210 represents a nonvolatile storage device represented by a hard disk, and stores various programs or data files executed by the signal processing unit 201. The reference numeral 202 represents a memory (RAM) disposed inside the signal processing unit 201. The reference numeral 203 represents a wavelength swept light source, and the wavelength swept light source serves as a light source for repeatedly generating the light having a wavelength, which varies within a preset range along a time axis.

In accordance with an exemplary embodiment, the light output from the wavelength swept light source 203 is incident on one end of a first single mode fiber 271, and is transmitted toward the distal side. The first single mode fiber 271 is optically coupled with a fourth single mode fiber 275 in an optical fiber coupler 272 located in an intermediate portion thereof.

The light incident on the first single mode fiber 271 and emitted to the distal side from the optical fiber coupler 272 is guided to a second single mode fiber 273 via the connector 105. The other end of the second single mode fiber 273 is connected to an optical rotary joint 230 inside the motor drive unit 102.

In accordance with an exemplary embodiment, the probe 101 has an adapter 101a for being connecting to the motor drive unit 102. Then, the probe 101 is connected to the motor drive unit 102 by using the adapter 101a, thereby stably holding the probe 101 in the motor drive unit 102. Furthermore, a third single mode fiber 274 is accommodated in the imaging core 251 accommodated inside the probe 101 so as to be rotatable, and an end portion of the third single mode fiber 274 is connected to the optical rotary joint 230. As a result, the second single mode fiber 273 and the third single mode fiber 274 are optically coupled to each other. The other end (front portion side of the probe 101) of the third single mode fiber 274 has an optical transceiver 250 (details will be described with reference to FIG. 3A) which is configured to include a mirror and a lens for emitting the light in a direction substantially orthogonal to the rotation axis.

As the above-described result, the light emitted by the wavelength swept light source 203 is guided to the optical transceiver 250 disposed in an end portion of the third single mode fiber 274 via the first single mode fiber 271, the second single mode fiber 273, and the third single mode fiber 274. The optical transceiver 250 emits the light in a direction orthogonal to the axis of the third single mode fiber 274, and receives the reflected light therefrom. Then, the reflected light received by the optical transceiver 250 is conversely guided this time, and is caused to return to the operation control apparatus 103.

In accordance with an exemplary embodiment, an end portion opposite to the fourth single mode fiber 275 coupled to the optical fiber coupler 272 has an optical path length adjusting mechanism 220 for finely adjusting an optical path length of the reference light. The optical path length adjusting mechanism 220 functions as optical path length changing means for changing the optical path length corresponding to variations in the length so that the variations in the length of each probe 101 can be absorbed, in a case where the probe 101 is exchanged. Therefore, a collimating lens 225 located at an end portion of the fourth single mode fiber 275 is disposed on a movable one-axis stage 224 as indicated by an arrow 226 which indicates the axial direction of the light.

Specifically, in a case where the probe 101 is exchanged, the one-axis stage 224 functions as optical path length changing means having a variable range of the optical path length which can absorb the variations in the optical path length of the probe 101. Furthermore, the one-axis stage 224 is also provided with a function as adjusting means for adjusting the offset. For example, even in a case where the distal end of the probe 101 is not in close contact with the surface of the biological tissue, the optical path length is finely changed by the one-axis stage. In this manner, a state of interfering with the reflected light from the surface position of the biological tissue can be set.

In accordance with an exemplary embodiment, the optical path length is finely adjusted by the one-axis stage 224, and the light reflected on the mirror 223 via a grating 221 and a lens 222 is guided again to the fourth single mode fiber 275. The light is mixed with the light obtained from the second single mode fiber 273 side in the optical fiber coupler 272, and is received by a photodiode unit (PD) 204 as the interference light.

The interference light received by the photodiode unit 204 in this way is subjected to photoelectric conversion, is amplified by an amplifier 205, and thereafter, is input to a demodulator 206. The demodulator 206 performs demodulation processing for extracting only a signal portion of the interference light, and an output thereof is input to an A/D converter 207 as an interference light signal.

For example, the A/D converter 207 samples 2048 points of the interference light signal at 90 MHz, and generates one line digital data (interference light data). In accordance with an exemplary embodiment, the reason that the sampling frequency is set to 90 MHz is on the assumption that approximately 90% of a wavelength sweep cycle (25 μsec) is extracted as the digital data having 2,048 points in a case where the wavelength sweep repetition frequency is set to 40 kHz. There is no particular limitation thereto.

The interference light data in units of lines generated by the A/D converter 207 is input to the signal processing unit 201, and is temporarily stored in the memory 202. Then, in the signal processing unit 201, the interference light data is frequency-decomposed by means of Fast Fourier Transform (FFT), thereby generating data in the depth direction (line data). The signal processing unit 201 constructs an optical cross-sectional image at each position inside the blood vessel, based on the line data, and outputs the image to the monitor 113 at a predetermined frame rate, in some cases.

The signal processing unit 201 is further connected to the optical path length adjusting drive unit 209 and the communication unit 208. The signal processing unit 201 performs control (optical path length control) of the position of the one-axis stage 224 via the optical path length adjusting drive unit 209.

The communication unit 208 is internally equipped with several drive circuits, and communicates with the motor drive unit 102 under the control of the signal processing unit 201. In accordance with an exemplary embodiment, a drive signal is supplied to the radial scanning motor in order to rotate the third single mode fiber by using the optical rotary joint inside the motor drive unit 102, a signal is received from an encoder unit 242 in order to detect the rotation position of the radial motor, and a drive signal is supplied to a linear drive unit 243 in order to pull the third single mode fiber 274 at predetermined speed.

The above-described processes in the signal processing unit 201 are also realized by causing a computer to execute a predetermined program.

In the above-described configuration, if the probe 101 is located at a diagnosis target blood vessel position (such as the renal artery) of a patient, a transparent flushing liquid is guided toward the distal end of the probe 101 through a guiding catheter by a user's operation, and is released into the blood vessel. The reason is to exclude the influence of blood. Then, if the user inputs an instruction to start scanning, the signal processing unit 201 drives the wavelength swept light source 203 so as to drive the radial scanning motor 241 and the linear drive unit 243 (hereinafter, a light irradiating and light receiving process performed by driving the radial scanning motor 241 and the linear drive unit 243 is referred to as scanning). As a result, wavelength sweep light is supplied from the wavelength swept light source 203 to the optical transceiver 250 in the distal end of the imaging core 251 through the above-described route. In this case, under the drive control of the motor drive unit 102, the imaging core 251 moves along the rotation axis while rotating. As a result, the optical transceiver 250 also moves along the blood vessel axis while rotating. The optical transceiver 250 emits the light to the vascular lumen surface, and receives the reflected light therefrom.

Figure 3A:
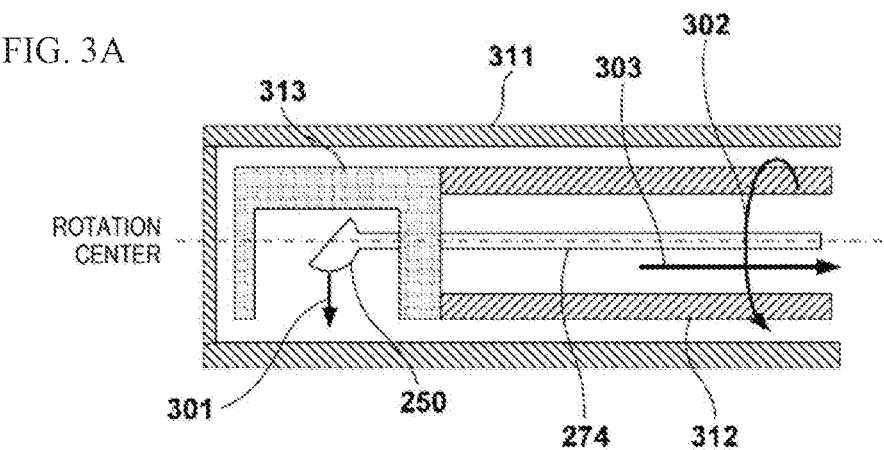
FIG. 3A is a view illustrating a cross-sectional configuration of a probe distal end.

FIG. 3A is a cross-sectional view of the probe 101 and the distal portion of the imaging core 251 accommodated in the probe 101. The distal portion of the probe 101 is configured to include a transparent catheter sheath 311 in order to transmit the light therethrough. The imaging core 251 is configured to include a drive shaft 312 for accommodating the third single mode fiber 274 and transmitting a rotation force (indicated by an arrow 302 in the drawing) from the motor drive unit 102, and a housing 313 for accommodating the optical transceiver 250 attached to a distal end thereof. The illustrated one-dot chain line is a rotation center axis. In addition, the motor drive unit 102 pulls the drive shaft 312 in a direction indicated by an arrow 303, thereby causing the optical transceiver 250 to move inside the catheter sheath 311. The optical transceiver 250 is configured to include a hemispherical ball lens as illustrated. According to this structure, a slope reflects the light incident from the third single mode fiber 274 in a substantially perpendicular direction (direction indicated by an arrow 301 illustrated in the drawing). As a result, the light is emitted toward the vascular tissue, and the reflected light therefrom is again transmitted to the third single mode fiber 274 via the lens.

Figure 3B:
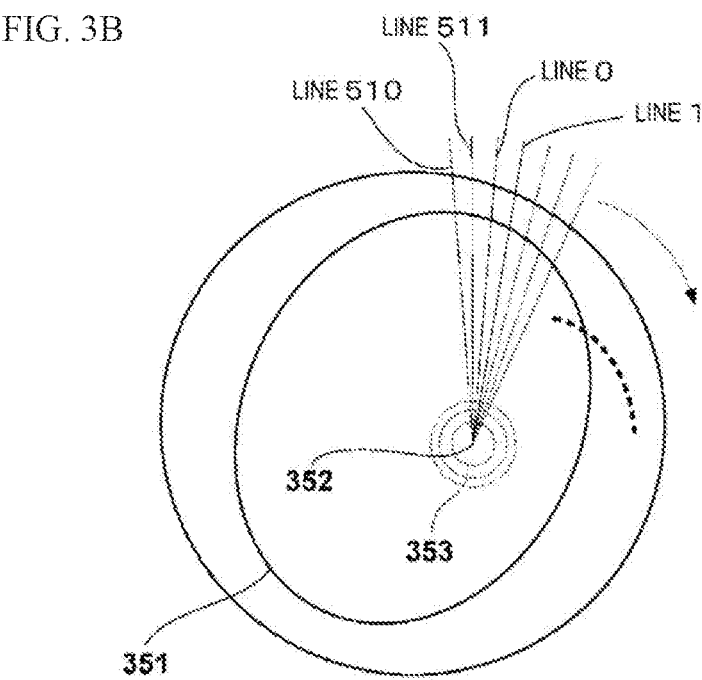
FIG. 3B is a view illustrating a process for generating a cross-sectional image.

In accordance with an exemplary embodiment, a process for generating one piece of optical cross-sectional image will be briefly described with reference to FIG. 3B. FIG. 3B is a view for describing a reconfiguration process of the cross-sectional image of a vascular lumen surface 351 of the blood vessel where the optical transceiver 250 is located. The measurement light is transmitted and received multiple times while one rotation the optical transceiver 250 is rotated once ($2\pi=360$ degrees). The wavelength swept light source 203 generates the light having a wavelength varying along the time axis during a period while the light is transmitted and received once by the optical transceiver 250. Therefore, the interference light data of one line in the light emitting direction is subjected to FFT processing by transmitting and receiving the light once. In this manner, it is possible to obtain "line data" indicating reflection intensity (or an absorbed amount) of the light at each position in the radial direction from the rotation center position. Therefore, for example, if the light is transmitted and received 512 times during one rotation, 512 pieces of line data extending radially from a rotation center 352 can be obtained.

These 512 pieces of line data are dense in the vicinity of the rotation center position, and become isolated from each other as the pieces move away from the rotation center position. Therefore, pixels in a vacant space between the respective lines are generated by performing well-known interpolation processing, thereby generating a two-dimensional cross-sectional image, which is visible to a person. In addition, the generated two-dimensional cross-sectional images are connected to each other along the blood vessel axis. In this manner, a three-dimensional blood vessel image can be obtained. It should be noted that the center position of the two-dimensional cross-sectional image coincides with the rotation center position of the optical transceiver 250, but is not the center position of the vascular cross section. In addition, although weak, the light is reflected on the lens surface of the optical transceiver 250, the inner surface of the catheter sheath 311, and each boundary surface of the outer surfaces. That is, three circles appear in the vicinity of the rotation center position. Among the circles, the innermost circle 353 is caused by light reflection on the lens surface of the optical transceiver 250.

Hitherto, basic configurations and functions of the imaging apparatus for diagnosis 100 according to the embodiment have been described. Next, detection of an ablation state by using the imaging apparatus for diagnosis 100 according to the embodiment will be described.

As described above, the cross-sectional images are obtained while the imaging core 251 is rotated and moved in the axial direction. In this manner, a series of a plurality of cross-sectional image groups are acquired along the direction of the blood vessel. Hereinafter, a method of calculating an ablation range and a depth by using the acquired cross-sectional image groups will be described. The calculation of the ablation range and the depth and a display process on the monitor described below can be realized by an image processing apparatus incorporated in or connected to the imaging apparatus for diagnosis 100. In the present embodiment, it is assumed that the function relating to the image processing apparatus is realized in such a way that a predetermined program is executed by a microprocessor included in the signal processing unit 201 of the imaging apparatus for diagnosis 100.

Figure 4:
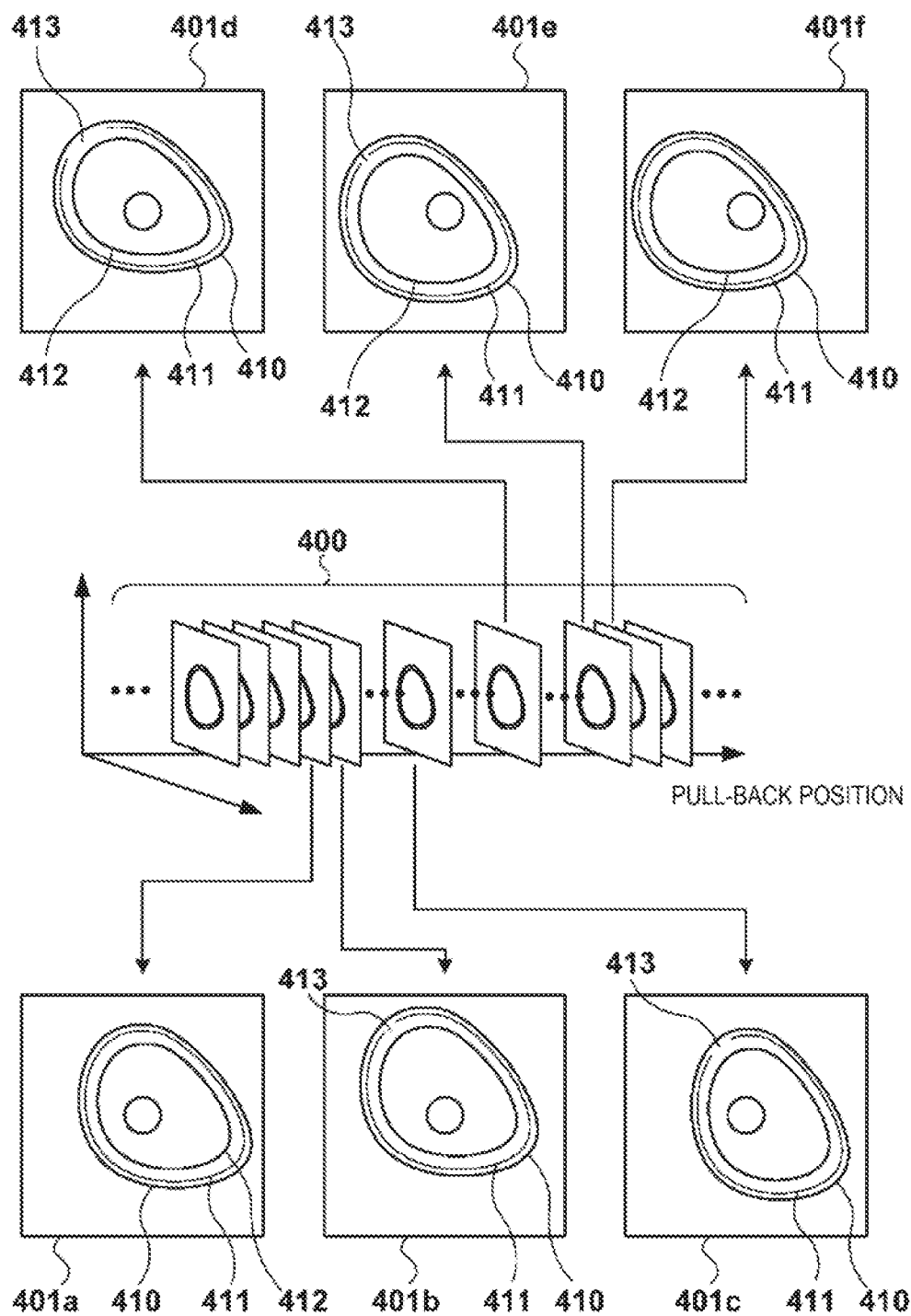
FIG. 4 is a view for describing a cross-sectional image group acquired using the imaging apparatus for diagnosis.

FIG. 4 is a view schematically illustrating the cross-sectional image groups obtained by moving the imaging core 251 in the axial direction inside the ablated renal artery. In this case, the plurality of cross-sectional images are arrayed along position information (hereinafter, referred to as a pull-back position) in the axial direction. For example, in a case where the linear drive unit 243 is configured to include a pulse motor, the pull-back position is obtained by counting drive pulses supplied to the pulse motor of the linear drive unit 243. However, the acquisition method of the pull-back position is not limited thereto. For example, the pull-back position may be acquired by disposing a linear scale moving in response to a position of an adapter and causing a sensor to read the position. Through the above-described processes, the pull-back position is added to each of the acquired cross-sectional image groups.

Each of the cross-sectional images configuring a cross-sectional image group 400 obtained in this way includes a vascular tomographic image of the renal artery, and the vascular lumen wall and the external elastic membrane can be observed from the vascular tomographic image. For example, in a cross-sectional image 401a, a continuous vascular lumen wall 412 and an external elastic membrane 411 are observed in a vascular tomographic image 410. In the renal artery, the sympathetic nerve runs outward from the external elastic membrane 411. Accordingly, in a case where the sympathetic nerve is ablated via the lumen wall, the thermal energy is applied to not only the sympathetic nerve but also the external elastic membrane present between the lumen wall and the sympathetic nerve. The external elastic membrane to which the thermal energy is applied is degenerated, and cannot be observed on the cross-sectional image (specifically, the external elastic membrane to which the thermal energy is applied is generated, and thus, a luminance value thereof decreases to such an extent that the external elastic membrane cannot be observed on the cross-sectional image). Therefore, if the ablation position is present in a movement range (imaging range) of the imaging core 251 in the axial direction, the external elastic membrane 411 partially disappears in the vascular tomographic image, thereby acquiring the cross-sectional image in which a discontinuous portion is present.

In the example of FIG. 4, a disappearance portion (discontinuous portion 413) is generated in the external elastic membrane 411 from the vascular tomographic image 410 of the cross-sectional image 401b. Thereafter, the discontinuous portion 413 is generated in the external elastic membrane 411 in cross-sectional images 401c, 401d, and 401e acquired while the pull-back position moves forward. In a cross-sectional image 401f, the discontinuous portion 413 no longer exists in the external elastic membrane 411. Therefore, in the example of FIG. 4, it is understood that the disappearance portion is generated in the external elastic membrane 411 in a section from the cross-sectional image 401b to the cross-sectional image 401e.

As described above, the pull-back position of the imaging core 251 is monitored, and the pull-back position can be identified when each of the cross-sectional images is acquired. Therefore, based on a difference between the pull-back positions of the cross-sectional image 401b where the disappearance portion of the external elastic membrane 411 starts and the cross-sectional image 401e where the disappearance portion of the external elastic membrane 411 ends, the length of the blood vessel having the disappearance portion of the external elastic membrane is recognized. In the present embodiment, this length and a model described below with reference to FIG. 5 are used so as to estimate a range influenced by the ablation (ablation range), thereby obtaining the ablation depth.

Figure 5:
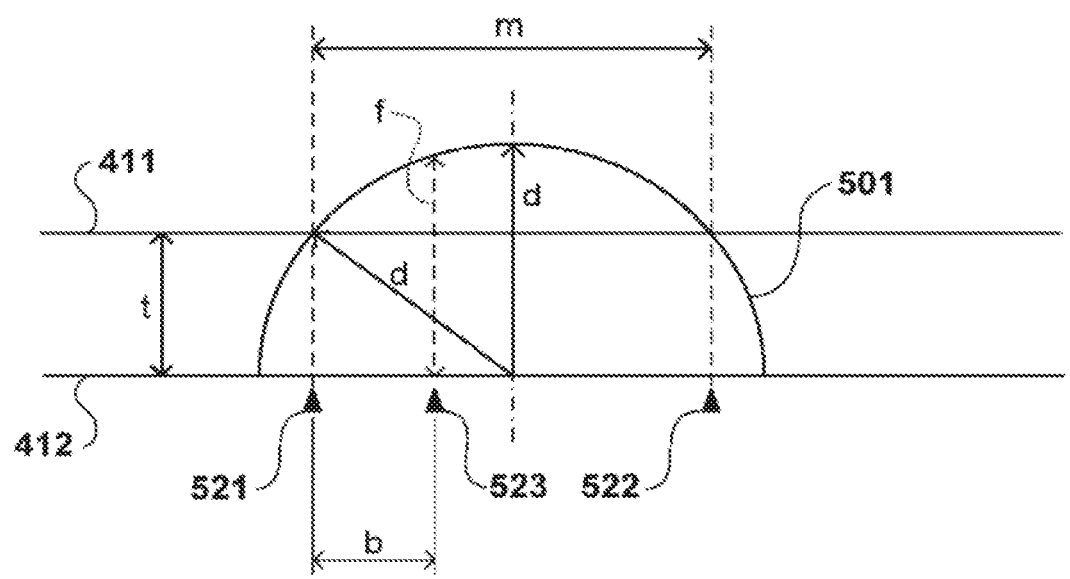
FIG. 5 is a view for describing a model for estimating an ablation range.

FIG. 5 is a view for describing the model for estimating the ablation range. First, a length m of the disappearance portion is obtained, based on the difference between a pull-back position 521 where the disappearance portion starts and a pull-back position 522 where the disappearance portion ends. In the example of FIG. 4, the difference between the pull-back position of the cross-sectional image 401b and the pull-back position of the cross-sectional image 401e is the length m of the disappearance portion. Then, in a case of a distance t from the vascular lumen (vascular lumen wall 412) to the external elastic membrane 411, a semicircle 501 which has a string of the length m at a position away from the center as far as the distance t and has a radius d is estimated as the ablation range. In addition, under the assumption that the ablation is performed in a state where the electrode of the ablation catheter is in contact with the inner surface of the vascular wall, the semicircle whose center is located on the inner surface of the vascular wall is estimated as the ablation range. In this case, the radius d is obtained by $d=\sqrt{(t^2+(m/2)^2)}$. The ablation range is modeled in this way. Accordingly, the ablation depth in any pull-back position inside the disappearance section can be calculated. For example, in a case of a difference b between the pull-back position 521 and a pull-back position 523, an ablation depth f at the pull-back position 523 is obtained by $f=\sqrt{(d^2-(m/2-b)^2)}$. In this manner, the ablation depth can be obtained for each of the cross-sectional images from the cross-sectional image 401b to the cross-sectional image 401e in FIG. 4.

The distance t from the vascular lumen (inner wall surface) of the blood vessel to the external elastic membrane (EEM) can be measured from the portion where the disappearance portion of the external elastic membrane is not generated in the cross-sectional image. Various methods are conceivable as follows. For example, when the interference light data of one line is read outward from the lumen wall of the renal artery, a portion where a boundary is found for the first time so that the luminance value increases beyond a predetermined threshold is detected as the position of the external elastic membrane. Alternatively, the position of the external elastic membrane is detected after an edge is emphasized using a Laplacian filter or a Sobel filter. The distance on the line between the position of the external elastic membrane and the position of the vascular lumen wall, which are determined using these methods, is set as t. Alternatively, an average distance (age group or gender may be used) of the external elastic membrane from the vascular lumen in the renal artery may be used.

Figure 6A:
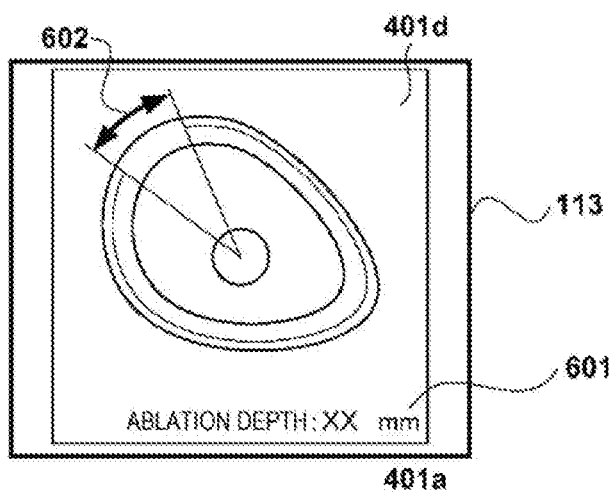
FIGS. 6A-6C are views describing a display of the cross-sectional image on a monitor in accordance with exemplary embodiments.
Figure 6B:
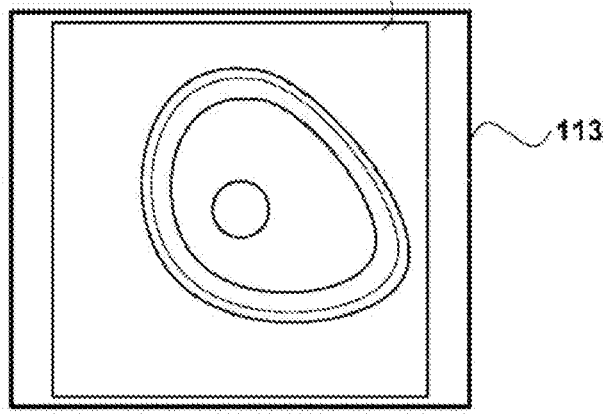
Figure 6C:
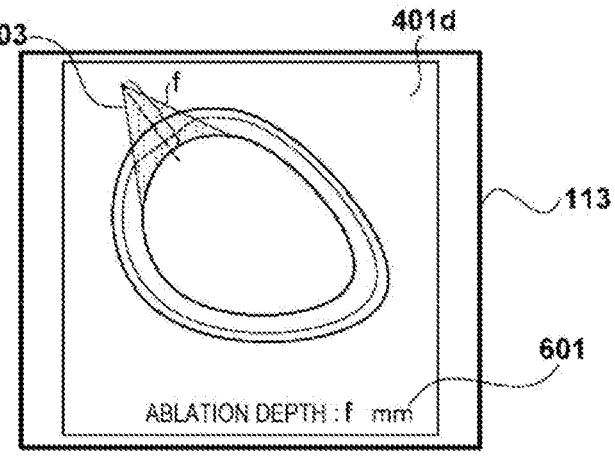

FIG. 6A illustrates an example of a state where a cross-sectional image 401d present in the disappearance section illustrated in FIG. 5 is displayed on the monitor 113. According to the above-described method, the ablation depth f at the pull-back position of the cross-sectional image 401d is calculated, and is displayed in a display area 601. In addition, based on a change in the luminance value, the ablation range in the circumferential direction is detected. For example, the detected ablation range in the circumferential direction is clearly indicated by an arrow 602. In addition to the configurations, as illustrated in FIG. 6C, a point having a depth f (f represents the ablation depth) from the lumen may be set on a perpendicular bisector of a line segment connecting both ends of the disappearance position of the external elastic membrane. In this manner, an ablation estimation range 603 may be displayed by connecting the point to both ends of the disappearance position and further extending the line to the lumen. As a method of connecting the point and both ends of the disappearance position, various methods such as linear and spline connection methods are conceivable. In accordance with an exemplary embodiment, as illustrated in FIG. 6B, in a case where the cross-sectional image (for example, the cross-sectional image 401a) outside the disappearance section is displayed on the monitor 113, the ablation depth is not displayed in the display area 601, or the arrow 602 indicating the ablation range in the circumferential direction is not displayed.

Figure 7:
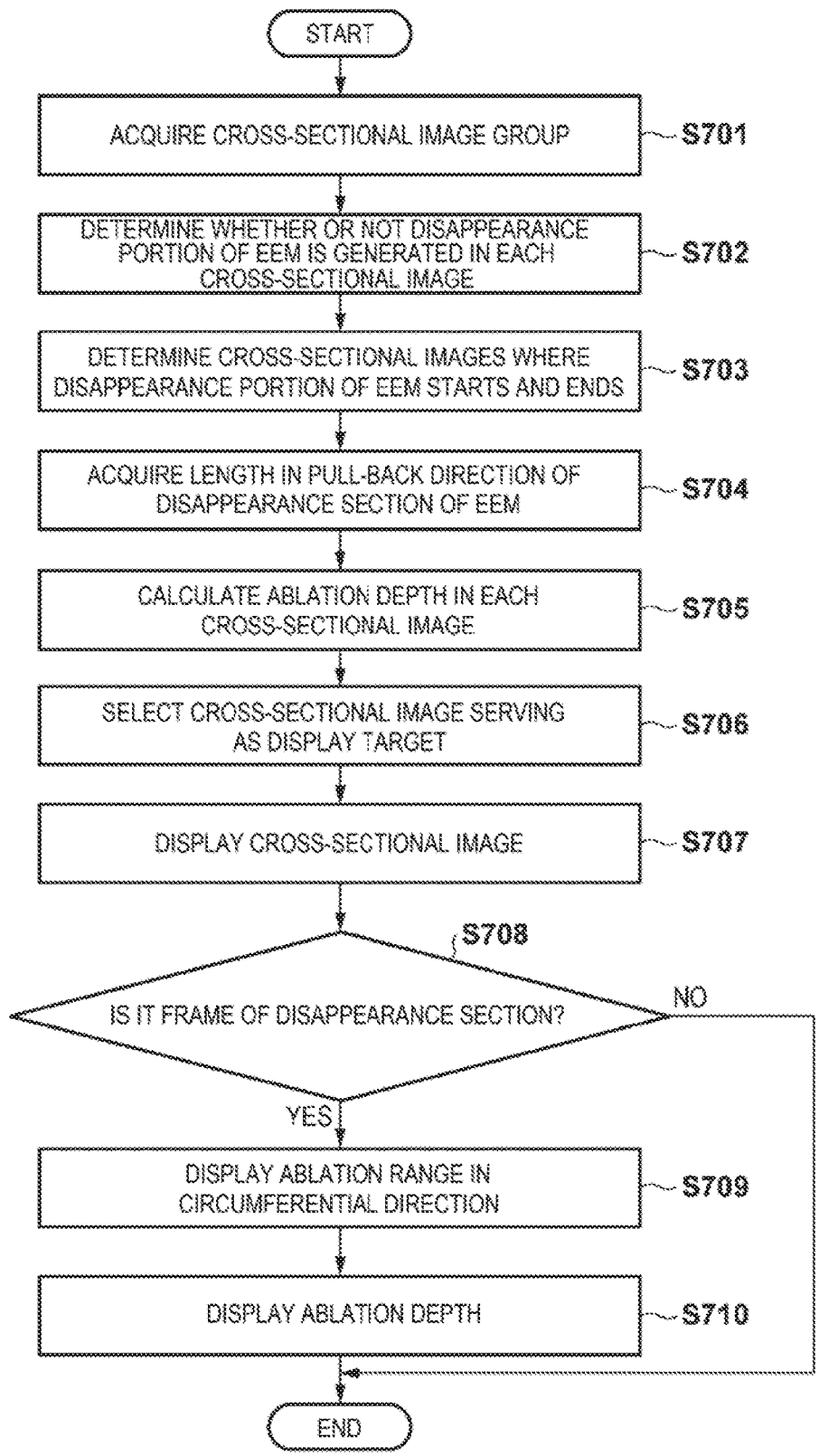
FIG. 7 is a flowchart for describing a process for estimating the ablation range according to the embodiment.

The above-described process will be described in more detail with reference to FIG. 7. FIG. 7 is a flowchart for describing a process relating to calculation and display of the ablation depth, in the processes executed by the microprocessor of the signal processing unit 201.

In Step S701, the microprocessor causes the imaging core 251 to move in the axial direction while causing the imaging core 251 to perform radial scanning, thereby acquiring the cross-sectional image group 400 including the plurality of cross-sectional images at the plurality of pull-back positions as described with reference to FIG. 4. FIG. 8 is a view for describing a configuration example of data acquired in Step S701. Each cross-sectional image of the cross-sectional image group 400 is stored in the memory 202 as frame data 801. At the time of Step S701, cross-sectional image data 802 corresponding to each cross-sectional image and a pull-back position 803 at the time of obtaining the cross-sectional image are recorded in the frame data 801.

Subsequently, in Step S702, the microprocessor determines whether or not the disappearance portion of the external elastic membrane is generated in each cross-sectional image group 400, and writes the determination result on an area (FIG. 8) of disappearance generation 804 of each frame data. The microprocessor detects the external elastic membrane for each cross-sectional image of the cross-sectional image group 400, and determines whether or not there is a disconnected portion (disappearance portion) in the external elastic membrane. Various methods are conceivable as follows. For example, a method is used in which when the interference light data of one line is read outward from the lumen wall of the renal artery, a portion where a boundary is found for the first time so that the luminance value increases beyond a predetermined threshold is detected as the position of the external elastic membrane. Alternatively, a method of detecting the position of the external elastic membrane after an edge is emphasized using a Laplacian filter or a line extracting filter. In a case where the position of the external elastic membrane specified using these methods is not within a specific depth range on the line, it is determined that the external elastic membrane disappears. Each cross-sectional image may be displayed on the monitor 113, and a user may observe the cross-sectional image so as to determine whether or not the external elastic membrane disappears. In this case, if the user designates "the disappearance generation is present" on each cross-sectional image in the disappearance section, the operation amount of the user increases. Therefore, the user may designate the cross-sectional image where the disappearance portion starts and the cross-sectional image where the disappearance portion ends. In this manner, "the disappearance generation is present" may be automatically written on the cross-sectional images and the disappearance generation 804 in all of the cross-sectional images (frame data) present therebetween. For example, if the user determines the cross-sectional image 401b as the disappearance start and the cross-sectional image 401e as the disappearance end, the disappearance generation 804 in all of the cross-sectional images including the cross-sectional images 401b to 401e is set as "the disappearance generation is present".

Next, in Step S703, the microprocessor refers to the disappearance generation 804 of the frame data 801 arrayed in the order (acquisition order) of the pull-back positions, and identifies the cross-sectional image where the disappearance generation of the external elastic membrane starts and the cross-sectional image where the disappearance generation of the external elastic membrane ends. For example, in a portion where the frame data is continuous so that the disappearance generation 804 is "present", the leading frame data is set as the disappearance start, and the trailing frame data is set as the disappearance end. Thereafter, in Step S704, the microprocessor obtains the difference in the pull-back positions between the frame data where the disappearance of the external elastic membrane starts and the frame data where the disappearance of the external elastic membrane ends, thereby acquiring the distance of the disappearance section where the external elastic membrane partially disappears, that is, the length m of the disappearance portion. The pull-back positions are recorded in each frame data. Accordingly, the length m of the disappearance portion can be easily obtained using the pull-back positions.

Next, in Step S705, the microprocessor calculates the ablation range for each cross-sectional image in the disappearance section, by using the model described with reference to FIG. 5. Then, the microprocessor calculates the ablation depth at the pull-back position of each frame data (cross-sectional image), based on the ablation depth, and records the calculation result in an ablation depth 805 of the frame data. The calculation result is recorded in the ablation depth 805 for the frame data in which the disappearance generation 804 is "present".

Next, the microprocessor performs display control for displaying the cross-sectional image. First, in Step S707, if the cross-sectional image (frame data) serving as the display target is selected, the microprocessor displays the cross-sectional image on the monitor 113. At this time, in a case where the cross-sectional image serving as the display target is the cross-sectional image in the disappearance section of the external elastic membrane, the process proceeds from Step S709 to Step S710. The microprocessor determines the ablation range in the circumferential direction, based on the cross-sectional image, and the ablation range is displayed by the arrow 602 as illustrated in FIG. 6A. Then, in Step S710, the microprocessor reads the ablation depth 805 of the frame data, and displays the ablation depth 805 in the display area 601 as "the ablation depth". If the cross-sectional image serving as the display target is not the image in the disappearance section, the process ends as it is from Step S708. The above-described ablation range in the circumferential direction is not displayed, and the depth of the irradiation zone is not displayed. Instead, a display illustrated in FIG. 6B is obtained.

In accordance with an exemplary embodiment, the ablation catheter for cutting the sympathetic nerve and the probe 101 may be inserted into the renal artery at the same time, and OCT imaging may be repeatedly performed during the ablation using the ablation catheter. In this manner, the user may determine that the ablation is completed. In this case, for example, in a case where the maximum value (FIG. 5 (5d)) of the above-described ablation depth exceeds a predetermined value, the microprocessor determines that the ablation is completed, and notifies the user of the determination result.

In addition, in the above-described embodiment, the disappearance section includes a frame (the cross-sectional image 401b in FIG. 4) in which the disappearance portion starts to be generated, a frame (the cross-sectional image 401e in FIG. 4) immediately before the first frame in which the disappearance portion is not generated, and a frame therebetween. However, the configuration is not limited thereto. For example, the frame (the cross-sectional image 401a) immediately before the frame where the disappearance portion starts to be generated, the first frame (the cross-sectional image 401f) where the disappearance portion is not generated, and the frame therebetween may be set as the disappearance section.

In addition, after the position of the nerve in the renal artery is detected using the optical coherence tomography technique, the lumen wall of the renal artery may be ablated by inserting the ablation catheter for cutting the sympathetic nerve, and thereafter, OCT imaging may be performed by inserting the above-described probe 101. In this manner, the above-described ablation depth may be calculated. In this manner, the calculated ablation depth is mapped for the position information of the nerve of the renal artery. Accordingly, the ablation state of the sympathetic nerve of the renal artery can be more accurately determined.

The present disclosure is not limited to the above-described embodiments. Alterations and modifications and variations can be made in various ways without departing from the spirit or scope of the present disclosure. Accordingly, in order to publicize the scope of the present disclosure, the following claim is appended.

The detailed description above describes an image processing apparatus, an image processing method, and a program for processing an optical coherence tomographic image. The invention is not limited, however, to the precise embodiments and variations described. Various changes, modifications, and equivalents can be effected by one skilled in the art without departing from the spirit and scope of the invention as defined in the accompanying claims. It is expressly intended that all such changes, modifications, and equivalents which fall within the scope of the claims are embraced by the claims.

What is claimed is:

1. An image processing apparatus for using OCT to process a plurality of cross-sectional images obtained by moving an imaging core inside a catheter in an axial direction while rotating the imaging core, the apparatus comprising:
   a processor configured to:
      store data relating to the cross-sectional images in association with position information in the axial direction when each of the cross-sectional images is acquired;
      extract a first cross-sectional image in which a disappearance section enabling determination that there is a disappeared portion of an external elastic membrane included in a vascular tomographic image starts, and a second cross-sectional image in which the disappearance section ends, in the plurality of cross-sectional images; and
      acquire the position information in the axial direction of the first cross-sectional image and the second cross-sectional image, and for calculating an ablation range influenced by ablation at a position associated with the disappearance section, based on a difference in the acquired position information in the axial direction; and
   wherein in a case where a distance from an intravascular wall to the external elastic membrane is set to t and a difference in the position information in the axial direction is set to m, the processor is configured to:
      set a semicircle having a string having a length m at a position away from the center as far as the distance t, as the ablation range.

2. The image processing apparatus according to claim 1, wherein the processor is configured to:
   calculate an ablation depth in each of the cross-sectional images, in the disappearance section, based on the semicircle.

3. The image processing apparatus according to claim 1, wherein the processor is configured to:
   receive a user's designation of the cross-sectional image in which the disappearance section starts and the cross-sectional image in which the disappearance section ends.

4. The image processing apparatus according to claim 1, wherein the processor is configured to:
   detect an image of the external elastic membrane in the vascular tomographic image from each of the plurality of cross-sectional images, and determine whether or not the external elastic membrane partially disappears in each of the cross-sectional images.

5. The image processing apparatus according to claim 1, wherein the processor is further configured to:
   notifying a user that ablation is completed, in a case where the ablation depth extracted by the extraction means exceeds a predetermined value.

6. The image processing apparatus according to claim 1, further comprising:
   a display configured to display the cross-sectional image selected in a case where the cross-sectional image belonging to the disappearance section is selected as a display target.

7. An image processing apparatus for using OCT to process a plurality of cross-sectional images obtained by moving an imaging core inside a catheter in an axial direction while rotating the imaging core, the apparatus comprising:
   a processor configured to:
      store data relating to the cross-sectional images in association with position information in the axial direction when each of the cross-sectional images is acquired;
      extract a first cross-sectional image in which a disappearance section enabling determination that there is a disappeared portion of an external elastic membrane included in a vascular tomographic image starts, and a second cross-sectional image in which the disappearance section ends, in the plurality of cross-sectional images; and
      acquire the position information in the axial direction of the first cross-sectional image and the second cross-sectional image, and for calculating an ablation range influenced by ablation at a position associated with the disappearance section, based on a difference in the acquired position information in the axial direction; and
   a display configured to display the cross-sectional image selected in a case where the cross-sectional image belonging to the disappearance section is selected as a display target, and wherein the ablation depth is obtained from the calculated ablation range.

8. The image processing apparatus according to claim 7, wherein the processor is further configured to:
   detect the ablation range in a circumferential direction, based on a change in a luminance value of the selected cross-sectional image, and
   the display specifies the ablation range in the circumferential direction which is detected, in displaying the selected cross-sectional image.

9. The image processing apparatus according to claim 7, wherein the processor is further configured to:
   notifying a user that ablation is completed, in a case where the ablation depth extracted by the extraction means exceeds a predetermined value.

10. An image processing method for using OCT to process a plurality of cross-sectional images obtained by moving an imaging core inside a catheter in an axial direction while rotating the imaging core, the method comprising:
   storing data relating to the cross-sectional images in association with position information in the axial direction when each of the cross-sectional images is acquired;

extracting a first cross-sectional image in which a disappearance section enabling determination that there is a disappeared portion of an external elastic membrane included in a vascular tomographic image starts, and a second cross-sectional image in which the disappearance section ends, in the plurality of cross-sectional images; and acquiring the position information in the axial direction of the first cross-sectional image and the second cross-sectional image, and for calculating an ablation range influenced by ablation at a position associated with the disappearance section, based on a difference in the acquired position information in the axial direction; and wherein in a case where a distance from an intravascular wall to the external elastic membrane is set to t and a difference in the position information in the axial direction is set to m, further comprising:

setting a semicircle having a string having a length m at a position away from the center as far as the distance t, as the ablation range.

11. The image processing method according to claim 10, comprising:
calculating an ablation depth in each of the cross-sectional images, in the disappearance section, based on the semicircle.

12. The image processing method according to claim 10, comprising:
receiving a user's designation of the cross-sectional image in which the disappearance section starts and the cross-sectional image in which the disappearance section ends.

13. The image processing method according to claim 10, comprising:
detecting an image of the external elastic membrane in the vascular tomographic image from each of the plurality of cross-sectional images, and determine whether or not the external elastic membrane partially disappears in each of the cross-sectional images.

14. The image processing method according to claim 10, further comprising:
notifying a user that ablation is completed, in a case where the ablation depth extracted by the extraction means exceeds a predetermined value.

15. A non-transitory computer readable medium comprising a program to execute each step of the image processing method according to claim 10.

16. The image processing method according to claim 10, further comprising:
displaying the cross-sectional image selected in a case where the cross-sectional image belonging to the disappearance section is selected as a display target on a display.

17. An image processing method for using OCT to process a plurality of cross-sectional images obtained by moving an imaging core inside a catheter in an axial direction while rotating the imaging core, the method comprising:
storing data relating to the cross-sectional images in association with position information in the axial direction when each of the cross-sectional images is acquired;
extracting a first cross-sectional image in which a disappearance section enabling determination that there is a disappeared portion of an external elastic membrane included in a vascular tomographic image starts, and a second cross-sectional image in which the disappearance section ends, in the plurality of cross-sectional images;
acquiring the position information in the axial direction of the first cross-sectional image and the second cross-sectional image, and for calculating an ablation range influenced by ablation at a position associated with the disappearance section, based on a difference in the acquired position information in the axial direction;
displaying the cross-sectional image selected in a case where the cross-sectional image belonging to the disappearance section is selected as a display target on a display; and
obtaining the ablation depth from the calculated ablation range.

18. The image processing method according to claim 17, further comprising:
detecting the ablation range in a circumferential direction, based on a change in a luminance value of the selected cross-sectional image, and
the display specifies the ablation range in the circumferential direction which is detected, in displaying the selected cross-sectional image.

19. The image processing method according to claim 17, further comprising:
notifying a user that ablation is completed, in a case where the ablation depth extracted by the extraction means exceeds a predetermined value.

20. A non-transitory computer readable medium comprising a program to execute each step of the image processing method according to claim 17.

* * * * *